United States Patent [19]

Michno

[11] Patent Number: 4,471,046
[45] Date of Patent: Sep. 11, 1984

[54] 4-HYDROXYALKYL-SUBSTITUTED 3-PYRAZOLIDINONE ELECTRON TRANSFER AGENTS

[75] Inventor: Drake M. Michno, Webster, N.Y.

[73] Assignee: Eastman Kodak Company, Rochester, N.Y.

[21] Appl. No.: 584,228

[22] Filed: Feb. 27, 1984

Related U.S. Application Data

[62] Division of Ser. No. 520,085, Aug. 4, 1983.

[51] Int. Cl.$^3$ .................. G03C 5/30; C07D 403/00; C07D 231/00
[52] U.S. Cl. .................... 430/483; 548/364; 548/367
[58] Field of Search ............. 430/218, 440, 480, 483; 548/364, 367

[56] References Cited

U.S. PATENT DOCUMENTS

| | | | |
|---|---|---|---|
| 3,039,869 | 6/1962 | Rogers et al. | 430/218 |
| 3,221,023 | 11/1965 | De Marle | 548/367 |
| 3,247,201 | 4/1966 | De Marle et al. | 430/483 |
| 3,453,109 | 7/1969 | Lee | 430/440 |
| 4,076,529 | 2/1978 | Fleckenstein et al. | 430/223 |
| 4,209,580 | 6/1980 | McCreary et al. | 430/218 |

FOREIGN PATENT DOCUMENTS 542502 1/1942 United Kingdom .
2073734A 10/1981 United Kingdom .

OTHER PUBLICATIONS

*Research Disclosure*, vol. 161, Sep. 1977, Item 16139, p. 26.

Primary Examiner—Richard L. Schilling
Attorney, Agent, or Firm—Harold E. Cole

[57] ABSTRACT

Photographic elements, film units, processes and alkaline processing compositions are described wherein certain 4-hydroxyalkyl-substituted 3-pyrazolidinones are employed as electron transfer agents in black-and-white and color image transfer materials. The silver halide electron transfer agents or precursors thereof have the following formula:

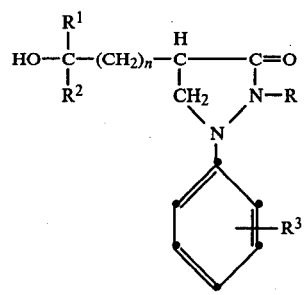

wherein:
n is 0, 1 or 2;
R represents hydrogen or a hydrolyzable moiety;
$R^1$ and $R^2$ each independently represents hydrogen, an alkyl or substituted alkyl group of 1 to about 6 carbon atoms, an aryl or substituted aryl group of 6 to about 10 carbon atoms, or an aralkyl group of 6 to about 10 carbon atoms, with the proviso that when n is 0, then either $R^1$ or $R^2$, but not both, may be hydrogen; and
$R^3$ represents at least one alkyl or alkoxy group having from 1 to about 6 carbon atoms, methylenedioxy group or ethylenedioxy group.

9 Claims, No Drawings

4-HYDROXYALKYL-SUBSTITUTED 3-PYRAZOLIDINONE ELECTRON TRANSFER AGENTS

This is a division of application Ser. No. 520,085, filed Aug. 4, 1983.

This invention relates to photography, and more particularly to black-and-white and color diffusion transfer photography wherein certain novel 4-hydroxyalkyl-substituted 3-pyrazolidinones are used as electron transfer agents. Post-processing $D_{min}$ stability is thereby greatly improved in accordance with this invention.

Various formats for color, integral transfer elements are described in the prior art, such as U.S. Pat. Nos. 3,415,644; 3,415,645; 3,415,646; 3,647,437; 3,635,707; 3,756,815, and Canadian Pat. Nos. 928,559 and 674,082. In these formats, the image-receiving layer containing the photographic image for viewing remains permanently attached and integral with the image generating and ancillary layers present in the structure when a transparent support is employed on the viewing side of the assemblage. The image is formed by dyes, produced in the image generating units, diffusing through the layers of the structure to the dye image-receiving layer. After exposure of the assemblage, an alkaline processing composition permeates the various layers to initiate development of the exposed photosensitive silver halide emulsion layers. The emulsion layers are developed in proportion to the extent of the respective exposures, and the image dyes which are formed or released in the respective image generating layers begin to diffuse throughout the structure. At least a portion of the imagewise distribution of diffusible dyes diffuse to the dye image-receiving layer to form an image of the original subject.

Other so-called "peel apart" formats for color diffusion transfer assemblages are described, for example, in U.S. Pat. Nos. 2,983,606; 3,362,819 and 3,362,821. In these formats, the image-receiving element is separated from the photosensitive element after development and transfer of the dyes to the image-receiving layer has occurred.

U.S. Pat. No. 4,076,529 of Fleckenstein et al, issued Feb. 28, 1978, describes various color image transfer elements which employ nondiffusible, redox dye-releasing (RDR) compounds which are alkali-cleavable upon oxidation to release a diffusible color-providing moiety. An electron transfer agent (ETA) is oxidized as a function of development. The $ETA_{ox}$ then cross-oxidizes the RDR. The ETA compounds described therein include various pyrazolidinones, such as 1-phenoxy-3-pyrazolidinone, 1-phenyl-4,4-dimethyl-3-pyrazolidinone and 4-hydroxymethyl-4-methyl-1-phenyl-3-pyrazolidinone. It would be desirable to provide ETA's with better development rates or lower $D_{min}$'s than those of the prior art.

In color transfer assemblages employing nondiffusible positive-working redox dye-releasing (PRDR) compounds, a dye is released as an inverse function of development, i.e., dye is released by some mechanism in the nonexposed areas of the silver halide emulsion. Use of a negative-working silver halide emulsion in such a system will therefore produce a positive image in the image-receiving layer. Examples of such PRDR's are described in U.S. Pat. Nos. 4,139,379 and 4,139,389. The immobile compounds described in these patents are ballasted electron-accepting nucleophilic displacement (BEND) compounds. The BEND compound as incorporated in a photographic element is incapable of releasing a diffusible dye. However, during photographic processing under alkaline conditions, the BEND compound is capable of accepting at least one electron (i.e., being reduced from an incorporated reducing agent (IRA) and thereafter releases a diffusible dye. This occurs in the unexposed areas of the emulsion layer. In the exposed areas of the emulsion layer, however, the ETA reduces the silver halide and becomes oxidized. The $ETA_{ox}$ is then reduced by the IRA, thus preventing the IRA from reacting with the BEND compound. The BEND compound therefore is not substantially reduced and thus no dye is released in the exposed areas.

After processing the photographic element described above containing PRDR's, ETA remains after imaging in both the exposed and nonexposed areas. A problem which occurs is that the $D_{min}$ continues to increase over a period of time. This is sometimes described in the art as "post-processing density increase". It is believed that over a period of time, the ETA can slowly reduce the PRDR and cause this unwanted dye release. It would be desirable to provide ETA's which have better post-processing $D_{min}$ stability in PRDR systems.

U.K. Pat. No. 542,502 discloses 3-pyrazolidinones with the 4-position being monosubstituted. The particular substituent on the 4-position of the compounds of this invention is not disclosed in this patent, however. As will be shown by comparative tests hereafter, this substituent is one of the most important features of these novel compounds.

U.S. Pat. Nos. 3,039,869, 4,209,580, 3,247,201, U.K. Pat. No. 2,073,734 and *Research Disclosure*, Vol. 161, September 1977, Item 16139, page 26 also disclose various 3-pyrazolidinones with various substituents. Again, however, the particular monosubstituted substituent on the 4-position of the compounds of this invention is not disclosed in these references.

It would be desirable to provide improved ETA's that have good reactivity, relatively low stain, lower $D_{min}$'s, better development rates, good stability in highly alkaline processing compositions (i.e., do not crystallize from or decompose in these compositions) and yet which will provide an improvement in post-processing $D_{min}$ stability, over those of the prior art.

These and other advantages are provided by the 4-hydroxyalkyl-substituted 3-pyrazolidinone compounds of this invention which are silver halide ETA's or precursors thereof and which have the following formula:

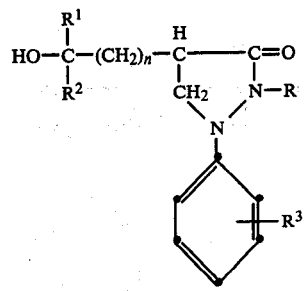

wherein:

n is 0, 1 or 2;

R represents hydrogen or a hydrolyzable moiety;

$R^1$ and $R^2$ each independently represents hydrogen, an alkyl or substituted alkyl group of 1 to about 6 carbon atoms such as methyl, ethyl, propyl, sec-butyl, hydroxyethyl, ethoxy, methoxy, N,N-dimethylaminoethyl or allyl; an aryl or substituted aryl group of 6 to about 10 carbon atoms such as phenyl, p-tolyl, 2,4-xylyl, p-methoxyphenyl, p-carbonamidophenyl or p-hydroxymethylphenyl; or an aralkyl group of 6 to about 10 carbon atoms such as benzyl or phenethyl; with the proviso that when n is 0, then either $R^1$ or $R^2$, but not both, may be hydrogen; and $R^3$ represents at least one alkyl or alkoxy group having from 1 to about 6 carbon atoms, such as methyl, ethyl, butyl, methoxy, ethoxy or propoxy; methylenedioxy group or ethylenedioxy group.

R in the above formula can be hydrogen or any hydrolyzable moiety well known to those skilled in the art, such as acetyl, mono-, di-, or trichloroacetyl radicals, perfluoroacyl, pyruvyl, alkoxyacyl, nitrobenzoyl, cyanobenzoyl, sulfonyl, sulfinyl, or a blocking group as disclosed in Mooberry and Archie U.S. Pat. No. 4,358,525.

When R in the above formula is hydrogen, the compound formula may be written in the keto form as:

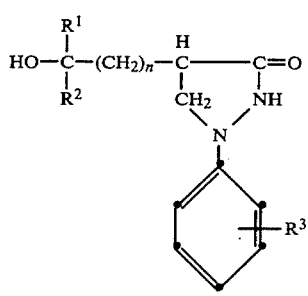

or in the enol form as:

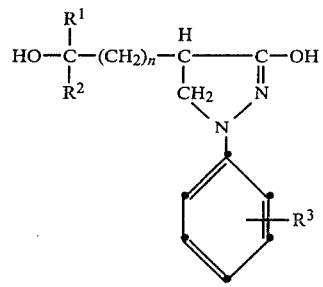

As used herein, the keto form is meant to include the enol form and vice versa.

When R in the above formula is a hydrolyzable moiety, then the compound is an ETA precursor and can be incorporated into a photographic element, cover sheet, receiving element, etc. Such compounds would be represented by the same general formula as above, except that "R" would be "$R^5$", wherein $R^5$ is a hydrolyzable moiety. During the processing of a photographic element containing an ETA precursor, $R^5$ will become hydrolyzed by the alkaline processing composition to become hydrogen. When used in this manner, the ETA precursor can be employed in any concentration effective for the intended purpose. Good results have been obtained when the ETA precursor is employed at a concentration of from about 0.05 to 2.0 mmoles/m² of element, preferably 0.1 to 1.5 mmoles/m².

ETA's directly incorporated into an alkaline processing composition will be subject to hydrolysis, so that R in the above formula intrinsically represents hydrogen. When employed in an alkaline processing composition, good results have been obtained when the ETA is present at a concentration of from about 0.1 to about 30 grams per liter, and preferably from about 2 to about 15 grams per liter.

In a preferred embodiment of this invention, $R^1$ is hydrogen or methyl. In another preferred embodiment of this invention, $R^2$ is hydrogen, methyl, isopropyl or phenyl. In yet another preferred embodiment of this invention, $R^3$ is methyl or methoxy located in the para-position.

In addition to $R^3$, the phenyl ring in the above formula may also be substituted with any substituent as long as the photographic activity of the ETA is not impaired. Such other substituents include, for example, chloro, benzyl, dialkylamino or alkoxycarbonyl.

Examples of compounds useful as an ETA or precursor thereof in accordance with this invention have the following formulae:

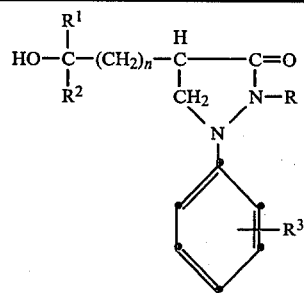

| Cmpd. No. | R | R¹ | R² | R³ | n |
| --- | --- | --- | --- | --- | --- |
| 1 | H | CH₃ | CH₃ | 4'-OCH₃ | 0 |
| 2 | H | CH₃ | CH₃ | 4'-CH₃ | 0 |
| 3 | H | H | CH(CH₃)₂ | 4'-CH₃ | 0 |
| 4 | H | H | C₆H₅ | 4'-CH₃ | 0 |
| 5 | H | CH₃ | C₆H₅ | 4'-CH₃ | 0 |
| 6 | H | H | CH₃ | 4'-CH₃ | 1 |
| 7 | H | H | H | 4'-OCH₃ | 1 |
| 8 | H | H | H | 4'-OCH₃ | 2 |
| 9 | H | H | H | 4'-CH₃ | 2 |
| 10 | H | CH₃ | CH₃ | 3',4'-OCH₂O— | 0 |
| 11 | H | CH₃ | C₆H₅ | 2'-OCH₃ | 0 |
| 12 | H | CH₂OH | CH₂OH | 4'-OCH₃ | 0 |
| 13 | H | CH₂OCH | CH₂OCH₃ | 4'-OCH₃ | 0 |
| 14 | CO₂C₄H₉ | H | C₆H₅ | 4'-CH₃ | 0 |
| 15 | COCH₃ | H | CH₃ | 4'-OCH₃ | 1 |
| 16 | CO₂CH₂C₆H₅ | H | CH₂ | 4'-OCH₃ | 1 |
| 17 | COCH₂C₆H₅ | H | H | 4'-CH₃ | 1 |
| 18 | CON(CH₃)—C₆H₄—o-COCH₂Cl | H | H | 4'-CH₃ | 1 |
| 19 | H | H | CH₃ | 4'-OCH₃ | 2 |
| 20 | CON(CH₃)—C₆H₄—o-CH₂N(CH₃)—COCF₃ | H | CH₃ | 4'-OCH₃ | 2 |
| 21 | H | H | C₆H₅ | 2'-OCH₃ | 0 |
| 22 | H | CH₃ | C₆H₅ | 2'-CH₃ | 0 |
| 23 | H | CH₃ | H | 3',4'-OCH₃ | 1 |
| 24 | H | C₂H₅ | H | 3',4'-CH₃ | 1 |

The ETA's described herein can be prepared by reaction of a substituted hydrazine with a β-halogenated or β-hydroxy acid chloride or carboxylic acid as shown in U.S. Pat. No. 2,289,367 and EP No. 55,900, the disclosures of which are hereby incorporated by reference. Another synthetic procedure involves transient blocking with a trialkylsilyl group, addition of the desired electrophile in the presence of a strong base, followed by removal of the blocking group by hydrolysis. This is described and claimed in Michno U.S. application Ser. No. 520,283, filed of even data herewith, entitled PREPARATION OF 4-SUBSTITUTED 3-PYRAZOLIDINONES, the disclosure of which is hereby incorporated by reference.

A photographic element according to this invention comprises a support having thereon at least one photosensitive silver halide emulsion layer having associated therewith a dye image-providing material, and containing an ETA precursor according to the formula above where R is a hydrolyzable moiety.

A dye image-receiving element according to this invention comprises a support having thereon a dye image-receiving layer and containing an ETA precursor according to the formula above where R is a hydrolyzable moiety.

A process for producing a photographic image in color according to this invention comprises: treating an imagewise-exposed photographic element, comprising a support having thereon at least one photosensitive silver halide emulsion layer having associated therewith a dye image-providing material, with an alkaline processing composition in the presence of a silver halide ETA to effect development of each exposed silver halide emulsion layer, whereby:

(a) an imagewise distribution of dye is formed as a function of the development of the silver halide emulsion layer; and
(b) at least a portion of the imagewise distribution of the dye diffuses out of the element, such as to a dye image-receiving layer.

In the above process, the ETA may be located in the alkaline processing composition or may be located in the photographic element (or in a cover sheet or receiving element) in its "blocked" precursor form.

It will be appreciated that, after processing the photographic element described above, there remains in the element, after transfer has taken place, an imagewise distribution of dye in addition to developed silver. A color image comprising residual nondiffusible compound may be obtained in this element if the residual silver and silver halide are removed in any conventional manner well known to those skilled in the photographic art, such as a bleach bath followed by a fix bath, a bleach-fix bath, etc. The imagewise distribution of dye may also diffuse out of this element into these baths, if desired, rather than to an image-receiving element.

The photographic element in the above-described process can be treated with an alkaline processing composition to effect or initiate development in any manner. A preferred method for applying processing composition is by use of a rupturable container or pod which contains the composition. The processing composition employed in this invention can contain the ETA for development, although the composition could also be solely an alkaline solution where the ETA is incorporated in the photographic element, the image-receiving element or the cover sheet. In these instances, the alkaline solution serves to activate the incorporated ETA.

A photographic assemblage or film unit in accordance with this invention is adapted to be processed by an alkaline processing composition, and comprises:
(1) a photographic element comprising a support having thereon at least one photosensitive silver halide emulsion layer having associated therewith a dye image-providing material; and
(2) a dye image-receiving layer, the assemblage containing the ETA or precursor thereof as described above. In this embodiment, the processing composition may be inserted into the film unit such as by interjecting processing solution with communicating members similar to hypodermic syringes which are attached either to a camera or camera cartridge. The processing composition may also be applied by means of a swab or by dipping in a bath, if so desired. In a preferred embodiment of the invention, the assemblage itself contains the alkaline processing composition and means containing same for discharge within the film unit, such as a rupturable container which is adapted to be positioned during processing of the film unit so that a compressive force applied to the container by pressure-applying members, such as would be found in a camera designed for in-camera processing, will effect a discharge of the container's contents within the film unit. As previously described, the ETA can be located in the assemblage in the processing composition. Alternatively, an ETA precursor can be located in the photographic element or in an image-receiving element, cover sheet or process sheet, as described previously.

The dye image-providing material useful in this invention is either positive- or negative-working, and is either initially mobile or immobile in the photographic element during processing with an alkaline composition. Examples of initially mobile, positive-working dye image-providing materials useful in this invention are described in U.S. Pat. Nos. 2,983,606; 3,536,739; 3,705,184; 3,482,972; 2,756,142; 3,880,658 and 3,854,985. Examples of negative-working dye image-providing materials useful in this invention include conventional couplers which react with oxidized aromatic primary amino color developing agents to produce or release a dye such as those described, for example, in U.S. Pat. No. 3,227,550 and Canadian Pat. No. 602,607. In a preferred embodiment of this invention, the dye image-providing material is a ballasted, redox-dye-releasing (RDR) compound. Such compounds are well known to those skilled in the art and are, generally speaking, compounds which will react with oxidized or unoxidized developing agent or electron transfer agent to release a dye. Such nondiffusible RDR's include negative-working compounds, as described in U.S. Pat. Nos. 3,728,113 of Becker et al; 3,725,062 of Anderson and Lum; 3,698,897 of Gompf and Lum; 3,628,952 of Puschel et al; 3,443,939 and 3,443,940 of Bloom et al; 4,053,312 of Fleckenstein; 4,076,529 of Fleckenstein et al; 4,055,428 of Koyama et al; 4,149,892 of Deguchi et al; 4,198,235 and 4,179,291 of Vetter et al; *Research Disclosure* 15157, November, 1976 and *Research Disclosure* 15654, April, 1977. Such nondiffusible RDR's also include positive-working compounds, as described in U.S. Pat. Nos. 3,980,479; 4,139,379; 4,139,389; 4,199,354, 4,232,107, 4,199,355 and German Pat. No. 2,854,946, the disclosures of which are hereby incorporated by reference.

In a preferred embodiment of this invention, positive-working quinone RDR's or PRDR's, are employed and the photographic element contains an incorporated reducing agent as described in U.S. Pat. No. 4,139,379, referred to above. In this embodiment, the quinone PRDR compound as incorporated in a photographic element is incapable of releasing a diffusible dye. However, during photographic processing under alkaline conditions, the compound is capable of accepting at least one electron (i.e., being reduced) and thereafter releases a diffusible dye. Further details are found in U.S. Pat. No. 4,139,379, the disclosure of which is hereby incorporated by reference. These quinone PRDR's have the formula:

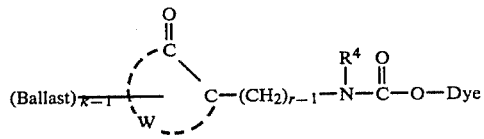

wherein:
Ballast is an organic ballasting radical of such molecular size and configuration as to render the compound nondiffusible in the photographic element during development in an alkaline processing composition;
W represents at least the atoms necessary to complete a quinone nucleus;
r is a positive integer of 1 or 2;
$R^4$ is an alkyl radical having 1 to about 40 carbon atoms or an aryl radical having 6 to about 40 carbon atoms;
k is a positive integer of 1 to 2 and is 2 when $R^4$ is a radical of less than 8 carbon atoms; and
Dye is an organic dye or dye precursor moiety.

In this invention, dye image-providing materials can be used which produce diffusible dye images as a function of development. Either conventional negative-working or direct-positive silver halide emulsions may be employed. If the silver halide emulsion employed is a direct-positive silver halide emulsion, such as an internal-image emulsion designed for use in the internal image reversal process, or a fogged, direct-positive emulsion such as a solarizing emulsion, which is developable in unexposed areas, a positive image can be obtained on the dye image-receiving layer by using ballasted, redox dye-releasers. After exposure of the film unit, the alkaline processing composition permeates the various layers to initiate development of the exposed photosensitive silver halide emulsion layers. The ETA present in the film unit develops each of the silver halide emulsion layers in the unexposed areas (since the silver halide emulsions are direct-positive ones), thus causing the ETA to become oxidized imagewise corresponding to the unexposed areas of the direct-positive silver halide emulsion layers. The oxidized ETA then cross-oxidizes the dye-releasing compounds and the oxidized form of the compounds then undergoes a base-catalyzed reaction to release the dyes imagewise as a function of the imagewise exposure of each of the silver halide emulsion layers. At least a portion of the imagewise distributions of diffusible dyes diffuse to the image-receiving layer to form a positive image of the original subject. After being contacted by the alkaline processing composition, a pH-lowering layer in the film unit or image-receiving unit lowers the pH of the film unit or image receiver to stabilize the image.

Internal-image silver halide emulsions useful in this invention are described more fully in the November 1976 edition of *Research Disclosure,* pages 76 through 79, the disclosure of which is hereby incorporated by reference.

The dye image-receiving layer in the above-described film assemblage is optionally located on a separate support adapted to be superposed on the photographic element after exposure thereof. Such image-receiving elements are generally disclosed, for example, in U.S. Pat. No. 3,362,819. In accordance with this embodiment of the invention, the dye image-receiving element would comprise a support having thereon, in sequence, a neutralizing layer, a timing layer and a dye image-receiving layer. When the means for discharging the processing composition is a rupturable container, it is usually positioned in relation to the photographic element and the image-receiving element so that a compressive force applied to the container by pressure-applying members, such as would be found in a typical camera used for in-camera processing, will effect a discharge of the container's contents between the image-receiving element and the outermost layer of the photographic element. After processing, the dye image-receiving element is separated from the photographic element.

In another embodiment, the dye image-receiving layer in the above-described film assemblage is located integral with the photographic element and is located between the support and the lowermost photosensitive silver halide emulsion layer. One useful format for integral imaging receiver photographic elements is disclosed in Belgian Patent No. 757,960. In such an embodiment, the support for the photographic element is transparent and is coated with an image-receiving layer, a substantially opaque light-reflective layer, e.g., TiO$_2$, and then the photosensitive layer or layers described above. After exposure of the photographic element, a rupturable container containing an alkaline processing composition and an opaque process sheet are brought into superposed position. Pressure-applying members in the camera rupture the container and spread processing composition over the photographic element as the film unit is withdrawn from the camera. The processing composition develops each exposed silver halide emulsion layer, and dye images, formed as a function of development, diffuse to the image-receiving layer to provide a positive, right-reading image which is viewed through the transparent support on the opaque reflecting layer background. For other details concerning the format of this particular integral film unit, reference is made to the above-mentioned Belgian Patent No. 757,960.

Another format for integral imaging receiver photographic elements in which the present invention is employed is disclosed in Canadian Pat. No. 928,559. In this embodiment, the support for the photographic element is transparent and is coated with the image-receiving layer, a substantially opaque, light-reflective layer and the photosensitive layer or layers described above. A rupturable container, containing an alkaline processing composition including an ETA and an opacifier, is positioned between the top layer and a transparent cover sheet which has thereon, in sequence, a neutralizing layer and a timing layer. The film unit is placed in a camera, exposed through the transparent cover sheet and then passed through a pair of pressure-applying members in the camera as it is being removed therefrom. The pressure-applying members rupture the container and spread processing composition and opacifier over the negative portion of the film unit to render it light-insensitive. The processing composition develops each silver halide layer and dye images, formed as a result of development, diffuse to the image-receiving layer to provide a positive, right-reading image which is viewed through the transparent support on the opaque reflecting layer background. For further details concerning the format of this particular integral film unit, reference is made to the above-mentioned Canadian Patent No. 928,559.

Still other useful integral formats in which this invention can be employed are described in U.S. Pat. Nos. 3,415,644; 3,415,645; 3,415,646; 3,647,437 and 3,635,707. In most of these formats, a photosensitive silver halide emulsion is coated on an opaque support and a dye image-receiving layer is located on a separate transparent support superposed over the layer outermost from the opaque support. In addition, this transparent support also contains a neutralizing layer and a timing layer underneath the dye image-receiving layer.

In another embodiment of the invention, the neutralizing layer and timing layer are located underneath the photosensitive layer or layers. In that embodiment, the photographic element would comprise a support having thereon, in sequence, a neutralizing layer, a timing layer and at least one photosensitive silver halide emulsion layer having associated therewith a dye image-providing material. A dye image-receiving layer would be provided on a second support with the processing composition being applied therebetween. This format could either be peel-apart or integral, as described above.

The film unit or assemblage of the present invention is used to produce positive images in single or multicolors. In a three-color system, each silver halide emulsion layer of the film assembly will have associated therewith a dye image-providing material which releases a dye possessing a predominant spectral absorption within the region of the visible spectrum to which said silver halide emulsion is sensitive, i.e., the blue-sensitive silver halide emulsion layer will have a yellow dye image-providing material associated therewith, the green-sensitive silver halide emulsion layer will have a magenta dye image-providing material associated therewith and the red-sensitive silver halide emulsion layer will have a cyan dye image-providing material associated therewith. The dye image-providing material associated with each silver halide emulsion layer is contained either in the silver halide emulsion layer itself or in a layer contiguous to the silver halide emulsion layer, i.e., the dye image-providing material can be coated in a separate layer underneath the silver halide emulsion layer with respect to the exposure direction.

The concentration of the dye image-providing material that is employed in the present invention can be varied over a wide range, depending upon the particular compound employed and the results desired. For example, a dye image-providing material coated in a layer at a concentration of 0.1 to 3 g/m² has been found to be useful. The dye image-providing material can be dispersed in a hydrophilic film-forming natural material or synthetic polymer, such as gelatin, polyvinyl alcohol, etc, which is adapted to be permeated by aqueous alkaline processing composition.

The various silver halide emulsion layers of a color film assembly employed in this invention can be disposed in the usual order, i.e., the blue-sensitive silver halide emulsion layer first with respect to the exposure side, followed by the green-sensitive and red-sensitive silver halide emulsion layers. If desired, a yellow dye layer or a yellow colloidal silver layer can be present between the blue-sensitive and green-sensitive silver halide emulsion layers for absorbing or filtering blue radiation that is transmitted through the blue-sensitive layer. If desired, the selectively sensitized silver halide emulsion layers can be disposed in a different order, e.g., the blue-sensitive layer first with respect to the exposure side, followed by the red-sensitive and green-sensitive layers.

The rupturable container employed in certain embodiments of this invention is disclosed in U.S. Pat. Nos. 2,543,181; 2,643,886; 2,653,732; 2,723,051; 3,056,492; 3,056,491 and 3,152,515. In general, such containers comprise a rectangular sheet of fluid-and air-impervious material folded longitudinally upon itself to form two walls which are sealed to one another along their longitudinal and end margins to form a cavity in which processing solution is contained.

Generally speaking, except where noted otherwise, the silver halide emulsion layers employed in the invention comprise photosensitive silver halide dispersed together with the dye image-providing material in gelatin or another aqueous alkaline solution-permeable polymeric binder and are about 0.6 to 7 microns in thickness; and the alkaline solution-permeable polymeric interlayers, e.g., gelatin, are about 0.2 to 5 microns in thickness. Of course, these thicknesses are approximate only and can be modified according to the product desired. The silver halide emulsions and dye releasers may also be coated in separate layers, if desired.

Scavengers for oxidized developing agents can be employed in various interlayers of the photographic elements of the invention. Suitable materials are disclosed on page 83 of the November 1976 edition of *Research Disclosure*, the disclosure of which is hereby incorporated by reference.

Any material is useful as the image-receiving layer in this invention, as long as the desired function of mordanting or otherwise fixing the dye images is obtained. The particular material chosen will, of course, depend upon the dye to be mordanted. Suitable materials are disclosed on pages 80 through 82 of the November, 1976 edition of *Research Disclosure*, the disclosure of which is hereby incorporated by reference.

Use of a neutralizing material in the film assemblages of this invention will usually increase the stability of the transferred image. Generally, the neutralizing material will effect a reduction in the pH of the image layer from about 13 or 14 to at least 11 and preferably 5 to 8 within a short time after treatment with alkali. Suitable materials and their functioning are disclosed on pages 22 and 23 of the July 1974 edition of *Research Disclosure*, and pages 35 through 37 of the July 1975 edition of *Research Disclosure*, the disclosures of which are hereby incorporated by reference.

A timing or inert spacer layer can be employed in the practice of this invention over the neutralizing layer which "times" or controls the pH reduction as a function of the rate at which alkali diffuses through the inert spacer layer. Examples of such timing layers and their functioning are disclosed in the *Research Disclosure* articles mentioned in the paragraph above concerning neutralizing layers.

The alkaline processing composition employed in this invention is the conventional aqueous solution of an alkaline material, e.g., alkali metal hydroxides or carbonates such as sodium hydroxide, sodium carbonate or an amine such as diethylamine, preferably possessing a pH in excess of 11, and preferably containing an ETA as described previously. Suitable materials and addenda frequently added to such compositions are disclosed on pages 79 and 80 of the November, 1976 edition of *Research Disclosure*, the disclosure of which is hereby incorporated by reference.

The alkaline solution permeable, substantially opaque, light-reflective layer employed in certain embodiments of photographic film units used in this invention is described more fully in the November, 1976 edition of *Research Disclosure*, page 82, the disclosure of which is hereby incorporated by reference.

The supports for the photographic elements used in this invention can be any material, as long as it does not deleteriously affect the photographic properties of the film unit and is dimensionally stable. Typical flexible sheet materials are described on page 85 of the November, 1976 edition of *Research Disclosure*, the disclosure of which is hereby incorporated by reference.

While the invention has been described with reference to layers of silver halide emulsions and dye image-providing materials, dotwise coating, such as would be obtained using a gravure printing technique, could also be employed. In this technique, small dots of blue-, green- and red-sensitive emulsions have associated therewith, respectively, dots of yellow, magenta and cyan color-providing substances. After development, the transferred dyes would tend to fuse together into a continuous tone. In an alternative embodiment, the emulsions sensitive to each of three primary regions of the spectrum can be disposed as a single segmented layer, e.g., as by the use of microvessels as described in Whitmore U.S. Pat. No. 4,362,806, issued Dec. 7, 1982.

The silver halide emulsions useful in this invention, both negative-working and direct-positive ones, are well known to those skilled in the art and are described in *Research Disclosure*, Volume 176, December, 1978, Item 17643, pages 22 and 23, "Emulsion preparation and types"; they are usually chemically and spectrally sensitized as described on page 23, "Chemical sensitization", and "Spectral sensitization and desensitization", of the above article; they are optionally protected against the production of fog and stabilized against loss of sensitivity during keeping by employing the materials described on pages 24 and 25, "Antifoggants and stabilizers", of the above article; they usually contain hardeners and coating aids as described on page 26, "Hardeners", and pages 26 and 27, "Coating aids", of the above article; they and other layers in the photographic elements used in this invention usually contain plasticizers, vehicles and filter dyes described on page 27, "Plasticizers and lubricants"; page 26, "Vehicles and vehicle extenders"; and pages 25 and 26, "Absorbing and scattering materials", of the above article; they and other layers in the photographic elements used in this invention can contain addenda which are incorporated by using the procedures described on page 27, "Methods of addition", of the above article; and they are usually coated and dried by using the various techniques described on pages 27 and 28, "Coating and drying procedures", of the above article, the disclosures of which are hereby incorporated by reference.

The term "nondiffusing" used herein has the meaning commonly applied to the term in photography and denotes materials that for all practical purposes do not migrate or wander through organic colloid layers, such as gelatin, in the photographic elements of the invention in an alkaline medium and preferably when processed in a medium having a pH of 11 or greater. The same meaning is to be attached to the term "immobile". The term "diffusible" as applied to the materials of this invention has the converse meaning and denotes materials having the property of diffusing effectively through the colloid layers of the photographic elements in an alkaline medium. "Mobile" has the same meaning as "diffusible".

The term "associated therewith" as used herein is intended to mean that the materials can be in either the same or different layers, so long as the materials are accessible to one another.

The following examples are provided to further illustrate the invention.

EXAMPLE 1

Photographic Test w/PRDR's (1) an acid layer comprising poly(n-butyl acrylate-co-acrylic acid), (30:70 weight ratio equivalent to 140 meq. acid/$m^2$); and
(2) a timing layer comprising a 1:1 physical mixture of the following two polymers coated at 4.8 g/$m^2$:
   (a) poly(acrylonitrile-co-vinylidene chloride-co-acrylic acid) (wt. ratio 14:79:7), and
   (b) a lactone polymer, partially hydrolyzed and 1-butanol transesterified poly(vinyl acetate-co-maleic anhydride) (ratio of acid/butyl ester 15:85).

(A) An integral imaging-receiver (IIR) element was prepared by coating the following layers in the order recited on a transparent poly(ethylene terephthalate) film support. Quantities ae parenthetically given in grams per square meter, unless otherwise stated.
(1) metal containing layer of nickel sulfate .6$H_2O$ (0.58) and gelatin (1.1);
(2) image-receiving layer of poly(4-vinylpyridine) (2.2) and gelatin (2.2);
(3) reflecting layer of titanium dioxide (16.0) and gelatin (2.6);
(4) opaque layer of carbon black (1.9) and gelatin (1.2);
(5) interlayer of gelatin (1.2);
(6) red-sensitive, negative-working silver bromoiodide emulsion (1.3 silver), gelatin (2.2), cyan PRDR-I (0.55), incorporated reducing agent IRA (0.29), and inhibitor (0.02); and
(7) overcoat layer of gelatin (0.87).

(B) Another element similar to (A) was prepared except that it contained cyan PRDR-II instead of cyan PRDR-I in layer 6.

Cyan PRDR-I

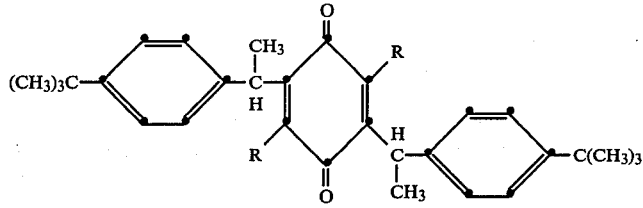

where R =

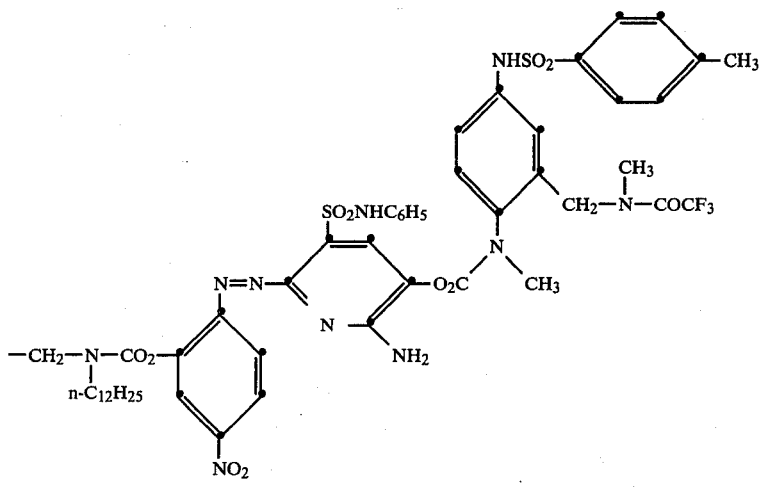

A cover sheet was prepared by coating the following layers, in the order recited, on a poly(ethylene terephthalate) film support:

Dispersed in di-n-butyl phthalate (PRDR-I:solvent 1:1)

Cyan PRDR-II

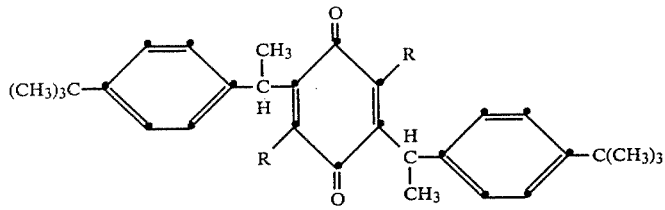

where R =

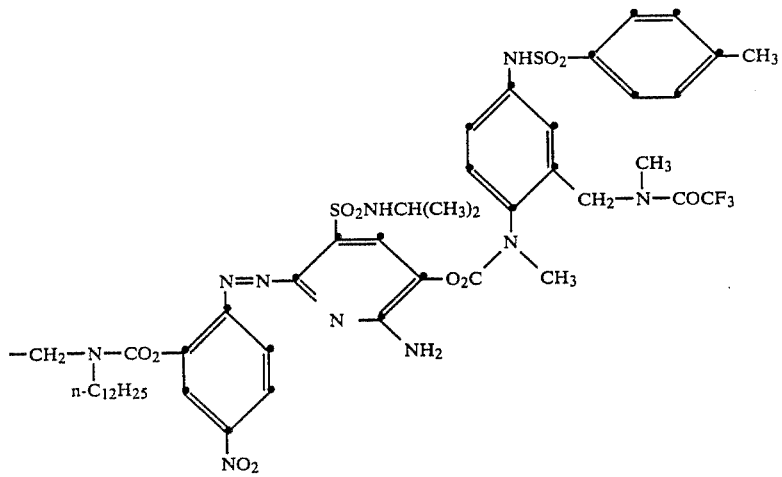

Dispersed in di-n-butyl phthalate (PRDR-II:solvent 1:1)

IRA

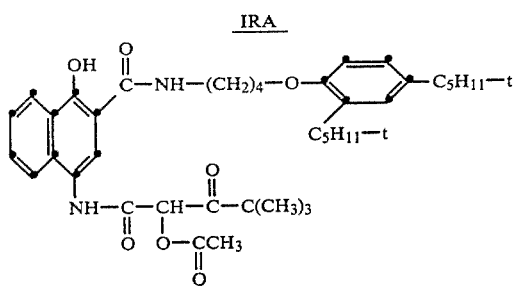

Dispersed in diethyllauramide (Total solid:solvent 1:1)

INHIBITOR

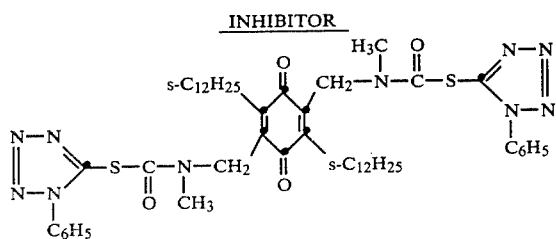

Dispersed in diethyllauramide (Total solid:solvent 1:1)

Pods containing the following processing composition were prepared:

|  | Pod Composition |
| --- | --- |
| Potassium hydroxide | 47.0 g |
| ETA (as specified in Table 1) | 0.02 M |
| 5-Methylbenzotriazole | 4.0 g |
| Sodium sulfite | 1.0 g |
| Carboxymethyl cellulose | 35.0 g |
| Water to 1 liter | |

Samples of the IIR containing either cyan PRDR-I or -II were exposed in a sensitometer through a graduated-density test object to yield a full-scale $D_{max}$-$D_{min}$ image after processing with the above viscous processing compositions in a pod. The exposed samples were processed at room temperature by rupturing a pod containing the viscous processing composition described above between the IIR and the cover sheet described above by using a pair of juxtaposed rollers at a gap of 100μ. Within 3 hours, the Status A red density of the receiver side of the IIR was read to give red $D_{max}/D_{min}$ data. After 48 hours incubation at 49° C./70% RH, the $D_{min}$ of the sample was read again. The $\Delta R$ $D_{min}$ increase indicates the extent of post-processing dye diffuson. The following results were obtained:

TABLE 1

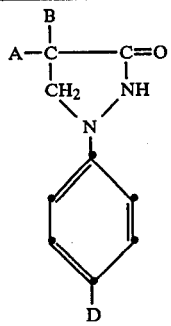

| ETA Compound | A | B | D | PRDR-I Initial Red Density $D_{min}$ | $D_{max}$ | 48 hr. @ 49° C. 70% RH $\Delta D_{min}$ | PRDR-II Initial Red Density $D_{min}$ | $D_{max}$ | 48 hr. @ 49° C. 70% RH $\Delta D_{min}$ |
|---|---|---|---|---|---|---|---|---|---|
| Control 1 | H | H | H | 0.18 | 1.04 | +0.50 | 0.76 | 2.10 | +0.26 |
| Control 2 | $CH_3$ | $CH_3$ | H | 0.50 | 1.24 | +0.59 | 1.23 | 1.82 | +0.36 |
| Control 3 | $CH_2OH$ | $CH_3$ | $CH_3$ | 0.18 | 0.74 | +46 | 0.14 | 1.56 | +0.20 |
| Control 4 | $CHOHCH_3$ | $CH_3$ | H | +0.20 | 1.00 | +0.44 | 0.54 | 2.00 | +0.20 |
| Control 5 | $CH_2CH_2OH$ | $CH_3$ | $CH_3$ | 0.14 | 0.74 | +0.70 | — | — | — |
| Control 6 | $C(OH)(CH_3)_2$ | H | H | — | — | — | 0.12 | 2.05 | +0.84 |
| 1 | $C(OH)(CH_3)_2$ | H | $OCH_3$ | — | — | — | 0.12 | 1.20 | +0.04 |
| 2 | $C(OH)(CH_3)_2$ | H | $CH_3$ | 0.10 | 0.32 | +0.12 | 0.16 | 2.15 | +0.03 |
| 3 | $CH(OH)CH(CH_3)_2$ | H | $CH_3$ | 0.10 | 0.44 | +0.15 | 0.12 | 1.24 | +0.10 |
| 4 | $CH(OH)C_6H_5$ | H | $CH_3$ | 0.18 | 1.12 | +0.11 | 0.24 | 1.94 | +0.05 |
| 5 | $C(OH)(CH_3)C_6H_5$ | H | $CH_3$ | 0.20 | 1.94 | +0.11 | 0.10 | 0.83 | 0 |
| 6 | $CH_2CHOHCH_3$ | H | $CH_3$ | 0.15 | 0.31 | +0.15 | 0.14 | 2.00 | +0.12 |
| 7 | $CH_2CH_2OH$ | H | $OCH_3$ | — | — | — | 0.13 | 1.18 | +0.07 |
| 8 | $(CH_2)_3OH$ | H | $OCH_3$ | — | — | — | 0.10 | 1.80 | +0.06 |
| 9 | $(CH_2)_3OH$ | H | $CH_3$ | — | — | — | 0.12 | 1.88 | +0.07 |

The above results indicate that the compounds according to the invention have much less post-processing dye diffusion (lower $\Delta D_{min}$ increases) than the control compounds which have closely related structures, such as 3-pyrazolidinones which are unsubstituted or disubstituted at the 4-position. A comparison of the results obtained with Compounds 1 and 2 with the results obtained with Control 6 also illustrates the effect of having an alkyl or alkoxy group on the phenyl ring.

EXAMPLE 2

Photographic Test w/Sulfonamidonaphthol RDR's

A cover sheet was prepared by coating the following layers, in the order recited, on a poly(ethylene terephthalate) film support:

(1) an acid layer comprising poly(n-butyl acrylate-co-acrylic acid), (30:70 weight ratio equivalent to 140 meq. acid/m²); and
(2) a timing layer comprising a mixture of cellulose acetate (40% acetyl) at 10.5 g/m² and poly(styrene-co-maleic anhydride) (50:50 wt. ratio) at 0.32 g/m². This layer also contained 0.11 g/m² of 5-(2-cyanoethylthio-1-phenyltetrazole.

An IIR element was prepared by coating the following layers in the order recited on a transparent poly(ethylene terephthalate) film support. Quantities are parenthetically given in grams per square meter, unless otherwise stated.

(1) image-receiving layer of a poly(styrene-co-N-benzyl-N,N-dimethyl-N-vinylbenzylammonium chloride-co-divinylbenzene) (molar ratio 49/49/2) (2.3) and gelatin (2.3);
(2) reflecting layer of titanium dioxide (16.2) and gelatin (2.6);
(3) interlayer of gelatin (0.54);
(4) magenta dye-providing layer of Magenta RDR (0.38) and gelatin (1.08);
(5) green-sensitive, direct-positive silver bromide emulsion (0.92 silver), gelatin (1.08), Nucleating Agent (0.002) and 2-(2-octadecyl)-5-sulfohydroquinone (0.14); and
(6) overcoat layer of gelatin (0.86).

The direct-positive emulsion was an approximately 0.8μ monodispersed, octahedral, internal image silver bromide emulsion, as described in U.S. Pat. No. 3,923,513.

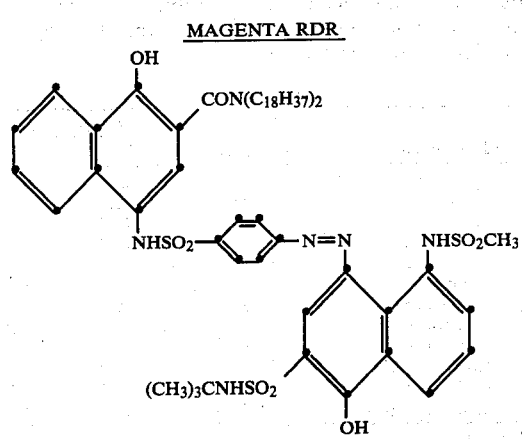

MAGENTA RDR

Dispersed in 1,4-cyclohexylenedimethyl bis(2-ethylhexanoate) (RDR:solvent 1:1)

Nucleating Agent

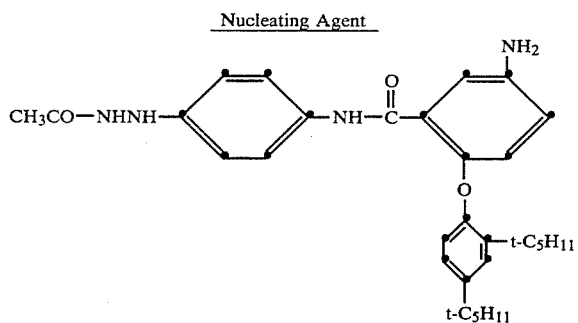

The magenta monochrome IIR was exposed in a sensitometer through a graduated density test object to yield a full-scale $D_{min}/D_{max}$ image after processing at 21° C. by rupturing a pod containing the viscous processing composition described below between the IIR element and the cover sheet described above, by using a pair of juxtaposed rollers to provide a processing gap of about 65 μm.

The processing composition was as follows:
Potassium hydroxide: 47.0 g
ETA (as specified in Table 2): 0.02M
5-Methylbenzotriazole: 4.0 g
Potassium sulfite: 1.0 g
Carboxymethylcellulose: 35.0 g
Water to 1 liter.

After a period of not less than an hour, the reflection density of the resulting image was read to obtain $D_{min}/D_{max}$ data.

Another sample of the IIR was left unexposed and processed in the dark to obtain maximum silver development of the internal image emulsion. The same pod, cover sheet, and lamination procedure was used as described above. Starting within 10 seconds after lamination, the infrared density at 920 nm was read at fixed time intervals from the receiver side of the IIR to obtain the relative rate of silver development as a function of time. The infrared density was read through the reflecting layer and through the dye that was released from the RDR and transferred to the receiver without significant interference. The time required to obtain one-half the total silver density (which is proportional to dye $D_{max}$) was determined. This relative development rate is a measure of the efficiency of the ETA to develop silver (with subsequent release of dye). The shorter the time, the more rapid and effective the development. The following results were obtained:

TABLE 2

| ETA Compound | Relative Development Rate | Green Density $D_{min}$ | $D_{max}$ |
|---|---|---|---|
| Control 1* | 39 | 0.23 | 1.6 |
| Control 2* | 45 | 0.20 | 2.0 |
| Control 3* | 22 | 0.22 | 1.6 |
| Compound 1 | 15 | 0.24 | 1.7 |
| Compound 2 | 22 | 0.22 | 1.3 |
| Compound 3 | 19 | 0.22 | 1.5 |
| Compound 4 | 23 | 0.20 | 1.5 |
| Compound 5 | 20 | 0.20 | 1.8 |
| Compound 6 | 29 | 0.20 | 1.5 |
| Compound 7 | 21 | 0.22 | 1.2 |
| Compound 8 | 16 | 0.20 | 1.1 |
| Compound 9 | 27 | 0.21 | 1.7 |

*See Example 1

The above results indicate that the ETA's of this invention have either a better relative development rate, an equal or lower $D_{min}$, or both, than the control ETA's and give adequate imaging (higher $D_{max}$ is obtainable through optimization).

EXAMPLE 3

Synthesis of Compound 2,4-(1-hydroxy-1-methylethyl)-1-p-tolyl-3-pyrazolidinone

To a stirred solution under nitrogen of 1-p-tolyl-3-pyrazolidinone (52.8 g, 0.30 mole) in 500 ml toluene and 50 ml anhydrous tetrahydrofuran was added sequentially t-butyl-dimethylsilyl chloride (49.5 g, 0.30 mole), triethylamine (33.0 g, 0.30 mole), 4-(N,N-dimethylamino)pyridine (0.1 g) and 1,8-diazabicyclo[5.4.0]-undec-7-ene (0.1 g). The mixture was refluxed for 3 hours, then cooled to 30° C., and filtered. After the solids were washed with ether, the solvents of the combined filtrate were removed under reduced pressure. The resulting solid was dissolved in 500 ml anhydrous ether and filtered to remove salts. Removal of the solvent of the filtrate yielded 85.6 g (98% yield) of 1-p-tolyl-3-(t-butyldimethylsiloxy)-2-pyrazoline.

A solution of 1-p-tolyl-3-(t-butyldimethylsiloxy)-pyrazoline (218 g, 0.75 mole) in 750 ml anhydrous tetrahydrofuran was added dropwise over a 30 minute period to a solution of n-butyllithium (51.5 g, 0.80 mole) in 350 ml n-hexane and 3.0 l anhydrous tetrahydrofuran stirred under nitrogen and cooled to −78° C. in a dry ice-acetone bath. The mixture was stirred for another 30 minutes then treated with one portion of acetone (58. g, 1.0 mole), and stirred at −78° C. for an additional 30 minutes. After removal of the dry ice-acetone bath, one portion of 250 ml 5% aqueous hydrochloric acid was added and the mixture was stirred an additional 25 minutes. The mixture was extracted with 1.0 l of ether and then with a (1:1) mixture of ether and ethyl acetate. The combined extracts were dried over magnesium sulfate. After removal of solvent, the residue was digested in a hot (3:2) mixture of ether and n-hexane. Upon cooling to 0° C. and filtering, 111 g of 4-(1-hydroxy-1-methylethyl)-1-p-tolyl-3-pyrazolidinone was obtained. Analysis was confirmed by infrared and NMR spectra.

EXAMPLE 4

Synthesis of Compound 9, 4-(3-hydroxypropyl-1-p-tolyl-3-pyrazolidinone

To a stirred room-temperature solution under nitrogen of t-butyldimethylsilyl chloride (49.7 g, 0.30 mole) and imidazole (51.0 g, 0.75 mole) in 100 ml N,N-dimethyl-formamide was added in one portion 3-bromo-propanol (41.7 g, 0.30 mole). The slightly exothermic reaction mixture was stirred for 3 hours, diluted with ice-water, and extracted three times with 200 ml portions of ether. The combined ether extracts were washed five times with 100 ml portions of water and dried over anhydrous magnesium sulfate. After removal of solvent, the residue was distilled under reduced pressure to yield 43.0 g of a clear oil, 3-bromo-1-(t-butyl-dimethylsiloxy)propane.

A solution of 1-p-tolyl-3-(t-butyldimethylsiloxy)-2-pyrazoline (11.6 g, 0.040 mole), prepared as in Example 3, in 80 ml anhydrous tetrahydrofuran was added dropwise over a 10 minute period to a stirred solution at −78° C. of lithium diisopropylamide in 50. ml anhydrous tetrahydrofuran under nitrogen (note: the lithium diisopropylamide was generated at 0° C. by mixing 5.1 g diisopropylamine and 3.2 g n-butyllithium in 21 ml of n-hexane). The resulting orange-red solution was allowed to stir for 30 minutes at −78° C., and was then treated with a single portion of 3-bromo-1-(t-butyldimethylsiloxy)propane (10. g, 0.040 mole) dissolved in 40. ml anhydrous tetrahydrofuran. After being allowed to warm to room temperature overnight, the mixture was diluted with 150 ml ether and 100 ml 10% aqueous hydrochloric acid and shaken vigorously. The separated aqueous layer was extracted with a (1:1) mixture of ether and ethyl acetate. The combined extracts were dried over magnesium sulfate. After removal of solvent the residue was chromatographed on a silica column and eluted with (70:30) hexane:ethyl acetate. A first fraction of 5.0 g (representing "4-monoalkylated" product), and third fraction of 2.8 g of product 4-(3-hydroxypropyl)-1-p-tolyl-3-pyrazolidinone were obtained. A second fraction of 1.0 g of "4,4-dialkylated" material was discarded. A total yield of 66% could be considered after hydrolysis of the first fraction.

The first fraction (1.5 g) was dissolved in 100 ml tetrahydrofuran, stirred under nitrogen at room temperature, and heated sequentially with 10 ml water and 0.5 ml trifluoroacetic acid. After two hours stirring the mixture was diluted with 200 ml ether, washed sequentially with water, ice cold saturated aqueous sodium bicarbonate, and saturated aqueous sodium chloride, and then dried over anhydrous magnesium sulfate. After removal of solvent, the oily resiude was chromatographed on a silica column and eluted with (80:20:2) methylene chloride, ether, ethanol. After recrystallization from 1:1 toluene and ether, 0.9 g of product 4-(3-hydroxypropyl)-1-p-tolyl-3-pyrazolidinone was obtained. Analysis was confirmed by NMR spectra.

The above synthesis examples are provided for illustration only and are claimed in Michno U.S. Application Ser. No. 520,283, filed of even date herewith, referred to above.

While specific utility for the compounds of this invention has been described for image transfer systems, these compounds would also be useful as developing agents in conventional black-and-white and color systems.

The invention has been described in detail with particular reference to preferred embodiments thereof, but it will be understood that variations and modifications can be effected within the spirit and scope of the invention.

What is claimed is:

1. An alkaline processing composition comprising a silver halide electron transfer agent having the following formula:

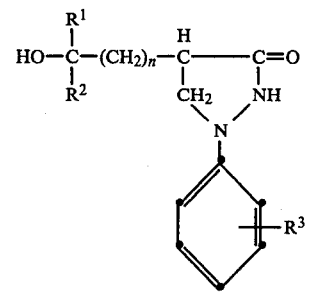

wherein:

n is 0, 1 or 2;

$R^1$ and $R^2$ each indpendently represents hydrogen, an alkyl or substituted alkyl group of 1 to about 6 carbon atoms, an aryl or substituted aryl group of 6 to about 10 carbon atoms, or an aralkyl group of 6 to about 10 carbon atoms, with the proviso that when n is 0, then either $R^1$ or $R^2$, but not both, may be hydrogen; and $R^3$ represents at least one alkyl or alkoxy group having from 1 to about 6 carbon atoms, methylenedioxy group or ethylenedioxy group.

2. The composition of claim 1 wherein $R^1$ is hydrogen or methyl.

3. The composition of claim 1 wherein $R^2$ is hydrogen, methyl, isopropyl or phenyl.

4. The composition of claim 1 wherein $R^3$ is either methyl or methoxy located in the para-position.

5. A silver halide electron transfer agent compound or precursor thereof having the following formula:

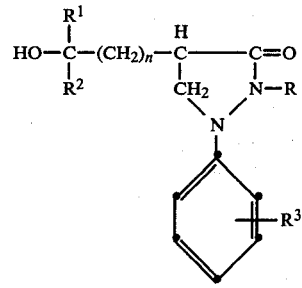

wherein:

n is 0, 1 or 2;

R represents hydrogen or a hydrolyzable moiety;

$R^1$ and $R^2$ each independently represents hydrogen, an alkyl or substituted alkyl group of 1 to about 6 carbon atoms, an aryl or substituted aryl group of 6 to about 10 carbon atoms, or an aralkyl group of 6 to about 10 carbon atoms, with the proviso that when n is 0, then either $R^1$ or $R^2$, but not both, may be hydrogen; and $R^3$ represents at least one alkyl or alkoxy group having from 1 to about 6 carbon atoms, methylenedioxy group or ethylenedioxy group.

6. The compound of claim 5 wherein R is hydrogen.

7. The compound of claim 6 wherein $R^1$ is hydrogen or methyl.

8. The compound of claim 6 wherein $R^2$ is hydrogen, methyl, isopropyl or phenyl.

9. The compound of claim 6 wherein $R^3$ is either methyl or methoxy located in the para-position.

* * * * *